(12) United States Patent
Inoue et al.

(10) Patent No.: US 11,944,281 B2
(45) Date of Patent: Apr. 2, 2024

(54) METHOD FOR TREATING GASTRO ESOPHAGEAL REFLUX DISEASE

(71) Applicant: OLYMPUS CORPORATION, Hachioji (JP)

(72) Inventors: Haruhiro Inoue, Tokyo (JP); Kunihide Kaji, Tokyo (JP); Yuji Kishimoto, Tokyo (JP); Nobuko Matsuo, Tokyo (JP); Yoshie Aikawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 840 days.

(21) Appl. No.: 17/071,050

(22) Filed: Oct. 15, 2020

(65) Prior Publication Data

US 2021/0045726 A1     Feb. 18, 2021

Related U.S. Application Data

(63) Continuation-in-part of application No. PCT/JP2020/000451, filed on Jan. 9, 2020, and a
(Continued)

(51) Int. Cl.
*A61B 17/00* (2006.01)
*A61B 18/00* (2006.01)
*A61B 18/14* (2006.01)

(52) U.S. Cl.
CPC .... *A61B 17/00234* (2013.01); *A61B 18/1492* (2013.01); *A61B 2017/00269* (2013.01);
(Continued)

(58) Field of Classification Search
CPC ......... A61B 17/00234; A61B 18/1492; A61B 2017/00269; A61B 2017/00827;
(Continued)

(56) References Cited

U.S. PATENT DOCUMENTS 6,197,026 B1    3/2001 Farin et al.
9,119,622 B2 *  9/2015 Rahmani .......... A61B 17/12013
(Continued)

FOREIGN PATENT DOCUMENTS

JP    H01-015362 Y2    5/1989
JP    H08-336542 A    12/1996
(Continued)

OTHER PUBLICATIONS

Jun. 6, 2023 Office Action issued in Japanese Patent Application No. 2021-570008.
(Continued)

*Primary Examiner* — William H Matthews
(74) *Attorney, Agent, or Firm* — Oliff PLC

(57) ABSTRACT

An endoscopic treatment method includes: inserting an endoscope into a digestive tract; forming a damaged area in at least a portion of the digestive tract along a circumferential direction by performing cauterizing while keeping a mucosal layer by observing with the endoscope; and forming an incomplete stenosis in the digestive tract, while restoring the damaged area, wherein the damaged area is formed by causing damage to a mucosal base layer, the mucosal base layer having an interface that contacts a submucosal layer.

9 Claims, 9 Drawing Sheets

Related U.S. Application Data continuation-in-part of application No. 16/279,381, filed on Feb. 19, 2019, now Pat. No. 10,835,222.

(52) U.S. Cl.
CPC ........... *A61B 2017/00827* (2013.01); *A61B 2018/00482* (2013.01); *A61B 2018/00488* (2013.01); *A61B 2018/00494* (2013.01); *A61B 2018/00577* (2013.01); *A61B 2018/00595* (2013.01); *A61B 2018/00738* (2013.01)

(58) Field of Classification Search
CPC ........... A61B 2018/00482; A61B 2018/00488; A61B 2018/00494; A61B 2018/00595; A61B 2018/00738
See application file for complete search history.

(56) References Cited

U.S. PATENT DOCUMENTS

| | | | |
|---|---|---|---|
| 9,592,070 | B2 | 3/2017 | Inoue |
| 2007/0066985 | A1* | 3/2007 | Geitz .................... A61B 10/06 606/170 |
| 2013/0090644 | A1 | 4/2013 | Williams et al. |
| 2015/0238219 | A1 | 8/2015 | Karwei |
| 2017/0071653 | A1* | 3/2017 | Enderle ................ A61B 18/042 |
| 2017/0312029 | A1* | 11/2017 | Schaer ..................... A61N 7/02 |

FOREIGN PATENT DOCUMENTS

| | | |
|---|---|---|
| JP | 2001-178740 A | 7/2001 |
| JP | 2002-503508 A | 2/2002 |
| JP | 2002-301088 A | 10/2002 |
| JP | 2003-534037 A | 11/2003 |
| JP | 2008-543355 A | 12/2008 |
| JP | 2015-062733 A | 4/2015 |
| JP | 2017-051615 A | 3/2017 |
| JP | 2017-153698 A | 9/2017 |
| WO | 2006/119892 A1 | 11/2006 |

OTHER PUBLICATIONS

Jan. 10, 2020 Office Action issued in U.S. Appl. No. 16/279,381.
Jul. 17, 2020 Notice of Allowance Issued in U.S. Appl. No. 16/279,381.
Mar. 24, 2020 International Search Report issued in International Patent Application No. PCT/JP2020/000451.
Feb. 9, 2021 International Search Report issued in International Patent Application No. PCT/JP2020/048466.
Mayo Tanabe et al., Sa1255, "A novel endoscopic fundoplication for gastroesophageal reflux disease; Anti-reflux mucosal ablation (ARMA)," Gastrointestinal Endoscopy, 2019, vol. 89, No. 6S, p. AB190.
Kazuya Sumi et al., "Esophageal hiatal hernia and GERD: New developments in endoscopic diagnosis and treatment," Endoscopia Digestiva, May 2020, vol. 32, No. 5, pp. 707-713.
Apr. 18, 2023 Office Action issued in Japanese Patent Application No. 2021-569661.

\* cited by examiner

METHOD FOR TREATING GASTRO ESOPHAGEAL REFLUX DISEASE

CROSS REFERENCE TO RELATED APPLICATIONS

This application is a continuation-in-part application based on a U.S. patent application Ser. No. 16/279,381, filed on Feb. 19, 2019, and also based on PCT Patent Application No. PCT/JP2020/000451, filed on Jan. 9, 2020. The contents of both applications are incorporated herein by reference.

BACKGROUND

Two types of possible treatments for gastro esophageal reflux disease (GERD) are (1) an oral treatment with a gastric acid secretion inhibitor, and (2) a surgical treatment such as laparoscopic Nissen fundoplication.

Oral treatment requires administration for a long time, and symptoms may not improve.

Surgical treatment can be solve the problem but is highly invasive. Since GERD is not a malignant disease such as a tumor, it is desirable that the treatment be minimally invasive.

A variety of endoscopic treatments are considered as options other than oral and surgical treatments. A procedure described in U.S. Pat. No. 9,592,070 is known as one of endoscopic treatments. In this procedure, the mucous membrane in the vicinity of the gastroesophageal junction is resected to cause scarring at the resected site and cause stenosis. As a result, reflux of stomach contents is suppressed.

SUMMARY

An exemplary embodiment of an endoscopic treatment method includes: inserting an endoscope into a digestive tract; forming a damaged area in at least a portion of the digestive tract along a circumferential direction by performing cauterizing while keeping a mucosal layer by observing with the endoscope; and forming an incomplete stenosis in the digestive tract, while restoring the damaged area, wherein the damaged area is formed by causing damage to a mucosal base layer, the mucosal base layer having an interface that contacts a submucosal layer.

DETAILED DESCRIPTION OF THE EMBODIMENTS

When performing an endoscopic treatment method for gastro esophageal reflux disease according to the present embodiment (hereinafter, simply referred to as "treatment method"), the operator first inserts an endoscope through a natural opening such as mouth or nose of the subject (insertion step), and moves the distal end of the endoscope into the stomach (digestive tract). As the endoscope, a known flexible endoscope can be used.

Figure 1:
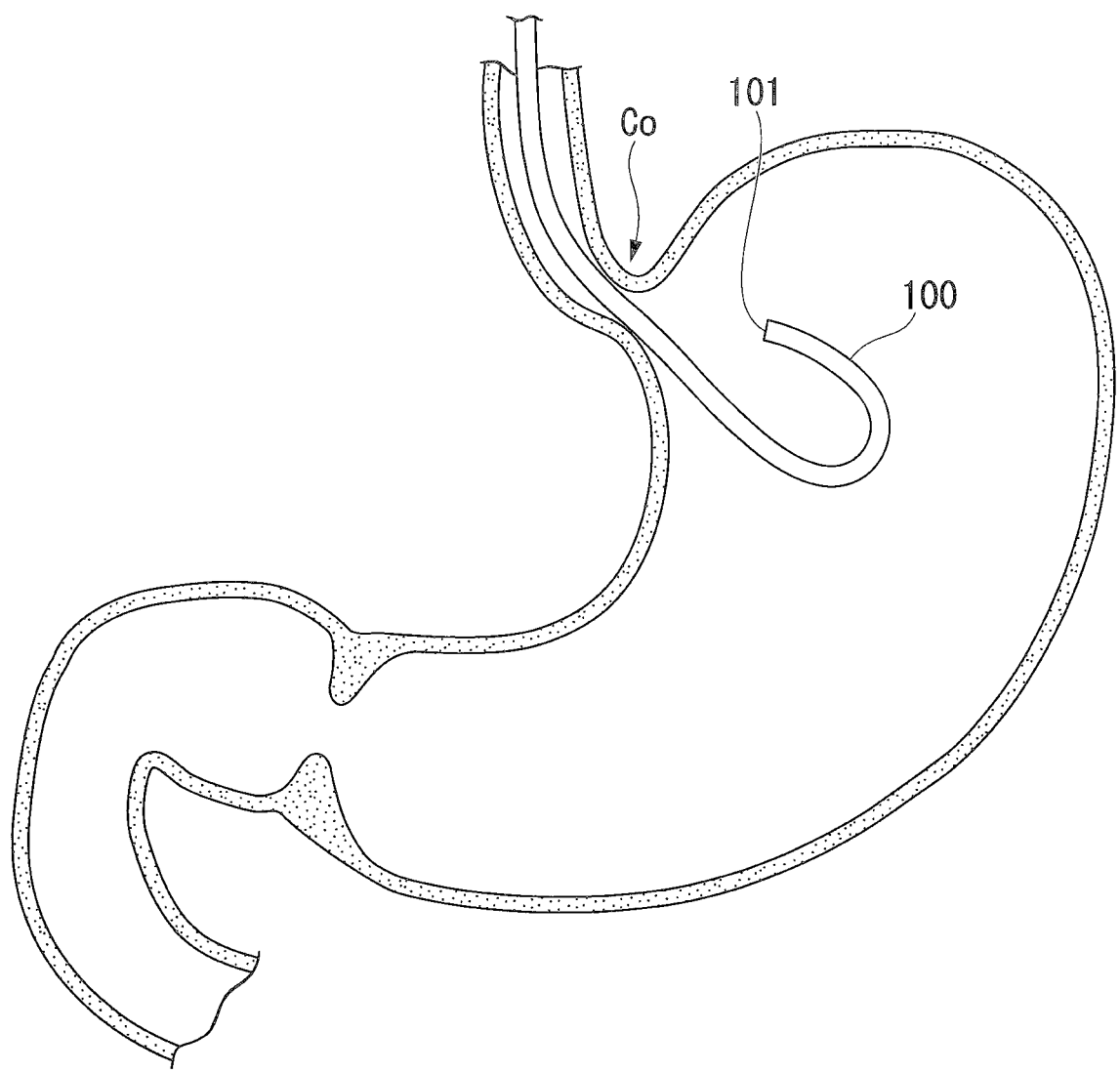
FIG. 1 is a view showing a state in which a gastroesophageal junction is observed with an endoscope inserted in the stomach.

Next, the operator operates the endoscope 100 to bend it. As shown in FIG. 1, the operator directs the distal end 101 of the endoscope 100 to the cardiac orifice Co, and captures the gastroesophageal junction around the cardiac orifice Co within the field of view of the endoscope 100. While observing the gastroesophageal junction, the operator determines a treatment area to be subjected to the cauterizing treatment described later (step A).

Figure 2:
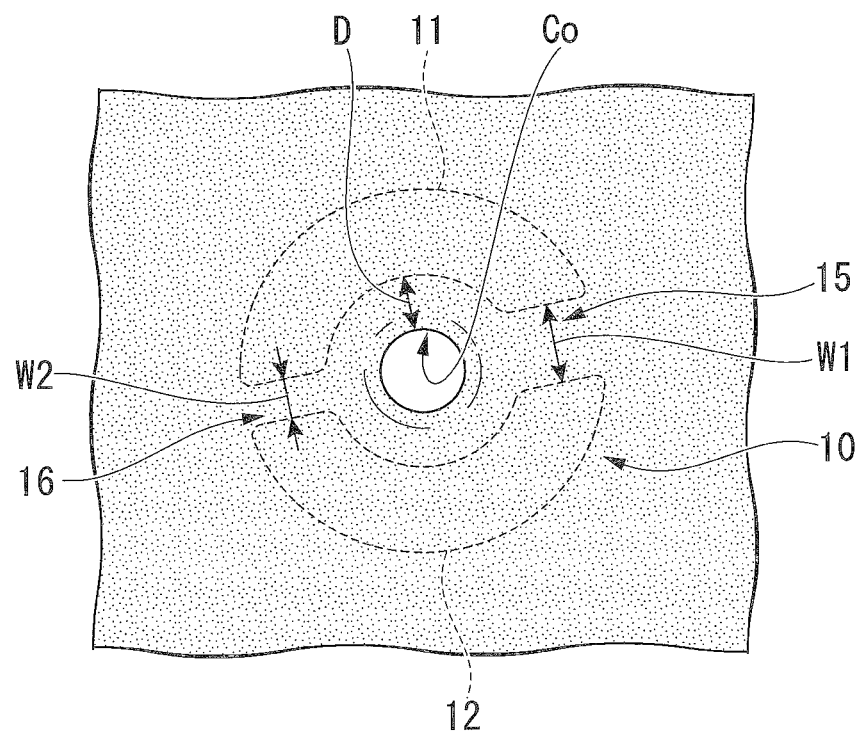
FIG. 2 is a view showing an example of a treatment area.

FIG. 2 shows an example of the treatment area. As shown in FIG. 2, the treatment area 10 has a shape in which a first area 11 and a second area 12 which are C-shaped or U-shaped face each other with a cardiac orifice Co interposed therebetween. The first area 11 is located on the anterior wall side of the stomach. The second area 12 is located on the posterior wall side of the stomach. The first area 11 and the second area 12 extend in the circumferential direction of the gastroesophageal junction.

By arranging the two sub-areas of the first area 11 and the second area 12 opposite to each other, the first boundary portion (first non-damaged area) 15 is located on the greater curvature side and the second boundary portion (second non-damaged area) 16 are located on the lesser curvature side, respectively. The first boundary portion 15 extends along the greater curvature. The second boundary 16 extends along the lesser curvature.

The width W1 of the first boundary portion 15 (the dimension in the circumferential direction of the gastroesophageal junction) is larger than the width W2 of the second boundary portion 16. For example, the width W1 is 10 to 20 millimeters, and the width W2 is 5 to 10 millimeters. In the following description, the first area 11 and the second area 12 may be collectively referred to as "sub-areas 11 and 12".

The sub-areas 11 and 12 are respectively separated from the cardiac orifice Co by a predetermined distance D. The predetermined distance D is, for example, 5 to 10 millimeters. The predetermined distance D of the first area 11 and the predetermined distance D of the second area 12 may not be the same.

The width of the sub-areas 11 and 12 extending in an arcuate shape along the circumferential direction of the gastroesophageal junction is, for example, 10 to 20 mm. The width may be constant or may vary depending on the site. Furthermore, the width of the first area 11 and the width of the second area 12 may be different.

Figure 3:
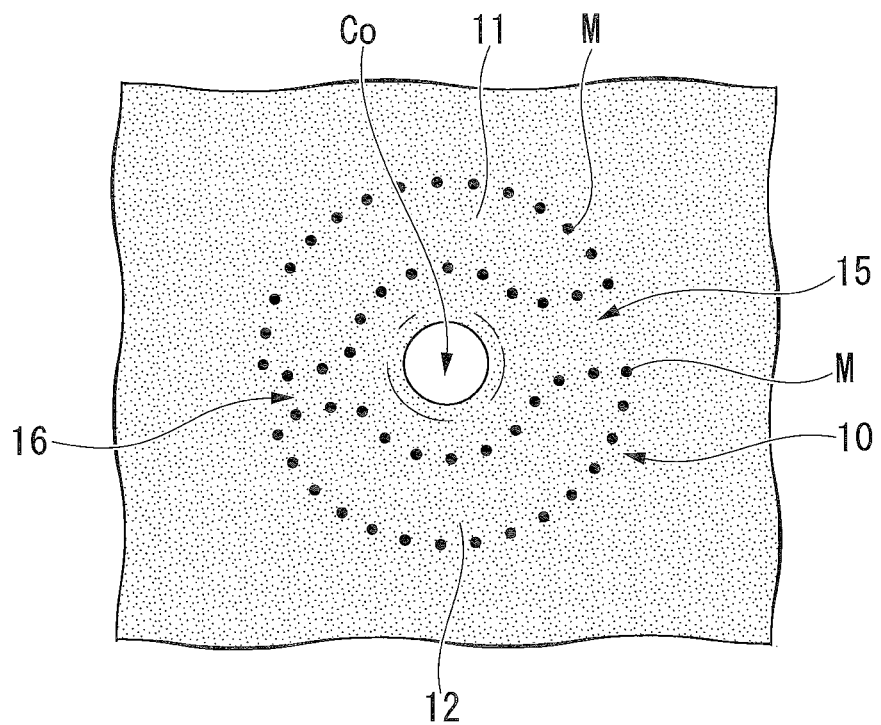
FIG. 3 is a view showing an example of a treatment area in which a marking is formed.

Next, the operator causes the treatment tool to protrude from the endoscope, and forms markings 20 around the treatment area 10 determined as shown in FIG. 3 using the treatment tool (step B). The markings 20 are formed by locally cauterizing the mucous membrane at the peripheral portions of the sub-areas 11 and 12. As a treatment tool for forming the markings 20, for example, a high frequency knife or a heat probe can be used.

The markings 20 need not be formed all around the treatment area, but may be formed at a plurality of spaced apart locations. In the treatment method of the present embodiment, since the first boundary portion 105 and the second boundary portion 106 play an important role, the markings 20 may be provided only around the first boundary portion 105 and the second boundary portion 106.

Figure 4:
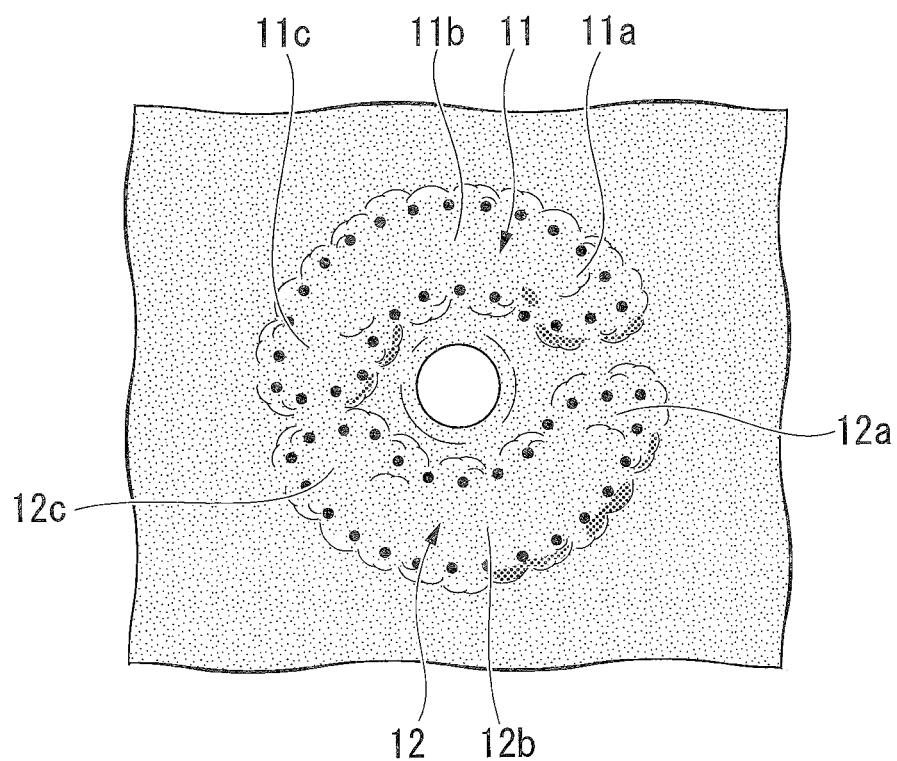
FIG. 4 is a view showing an example of a treatment area where swelled and lifted up.

Next, the operator injects a liquid into the submucosal layer of each of the sub-areas 11 and 12 to swell and lift up each of the sub-areas 11 and 12 as shown in FIG. 4 (step C). Saline solution or the like can be used as a liquid to inject. Since the degree of cauterizing can be easily grasped in a later step, it is preferable to color the liquid with a dye used in gastroscopes such as indigo blue or the like. The liquid can be injected using a local injection needle or the like for an endoscope.

When an endoscope having a plurality of channels is used in step C, replacement work of the treatment tool can be omitted by passing the local injection needle or the like and the treatment tool used for marking through different channels.

Figure 10:
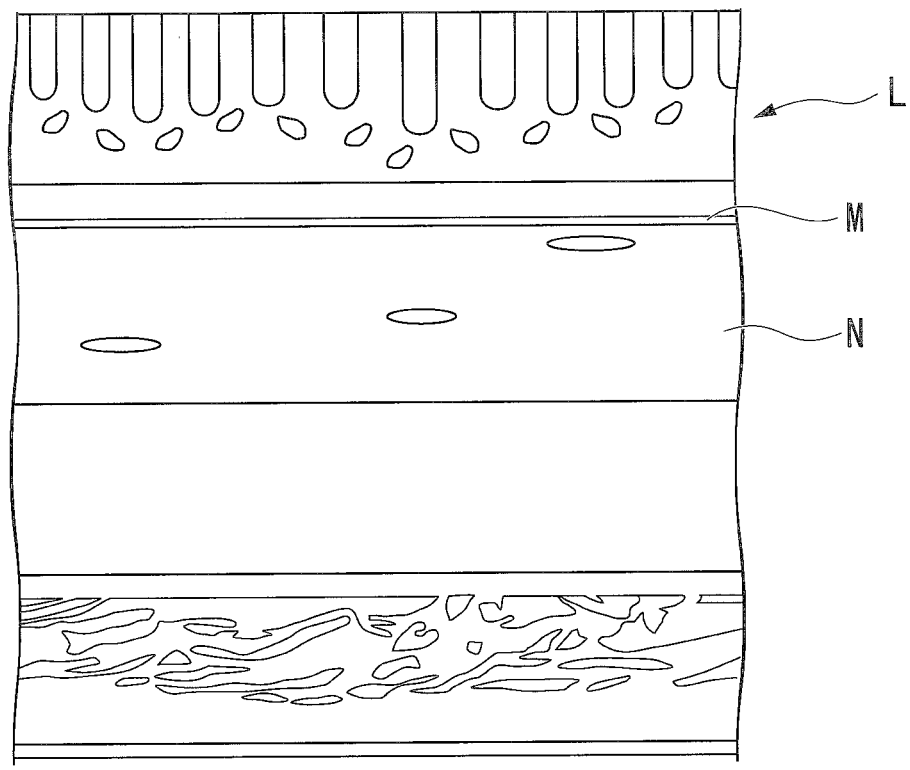
FIG. 10 is a schematic cross-sectional view of a stomach wall.

Next, the operator uses the treatment tool protruded from the endoscope to cauterize the portions 11a and 12a (see FIG. 4) which are close to the greater curvature side of the gastric mucosa in the sub-areas 11 and 12. The cauterizing is performed without excising the mucous membrane. The degree of cauterizing is such that the mucosal base layer is damaged. FIG. 10 shows a schematic cross-sectional view of the stomach wall. The mucosal base layer M is a part of the mucosal layer L and is a layer that includes an interface in contact with the submucosal layer N. It is also called basement membrane.

The portions 11a and 12a where swelled and lifted up have a positional relationship that makes it easy to face the endoscope due to the anatomical shape of the stomach bottom. Thereby, by advancing the treatment tool 150 while fixing the endoscope 100, the treatment tool 150 can be brought into contact with the mucous membrane of the target portions 11a and 12a as shown in FIG. 5.

Figure 5:
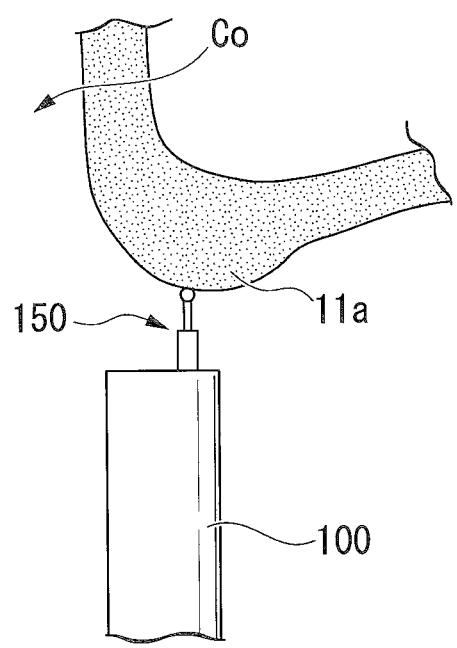
FIG. 5 is a view showing a state in which a treatment tool protruded from an endoscope is in contact with a portion close to a greater curvature side of the treatment area.

When a high-frequency knife is used as the treatment tool 150, the treatment tool 150 may be retracted little by little without moving the endoscope 100 from the state shown in FIG. 5 in which the distal end of the treatment tool 150 of which power supply is set to a coagulation mode is lightly pressed on the mucous membrane, and the cauterizing may be performed at the timing when the distal end is separated from the mucous membrane. When treated according to such a procedure, the discharge from the distal end can be used to suitably cauterize the mucous membrane. This is an example of a cauterizing procedure, and cauterizing may be performed in other procedures.

The operator cauterize the entire mucous membrane in the portions 11a and 12a by repeating cauterizing while twisting or bending the endoscope 100 to change the position of the distal end of the treatment tool 150. Since the portions 11a and 12a are close to the stomach bottom, this step cauterizes the area on the stomach bottom side of the treatment area 10.

Next, the operator uses the treatment tool protruded from the endoscope to cauterize the portions 11b and 12b closer to the anterior and posterior walls and the portions 11c and 12c (see FIG. 4) closer to the lesser curvature side of the gastric mucosa in the sub-areas 11 and 12. Also in this case, it should be noted that only cauterizing is performed without excising the mucous membrane. The treatment tool to be used may be the same as cauterizing of the portions 11a and 12a.

The portions 11b, 12b and 11c, 12c are difficult to face the endoscope 100 even if they are swelled and lifted up due to the anatomical shape of the stomach. As a result, the treatment tool 150 protruding from the endoscope 100 approaches the mucous membrane in a state parallel or nearly parallel to the stomach wall.

Figure 6:
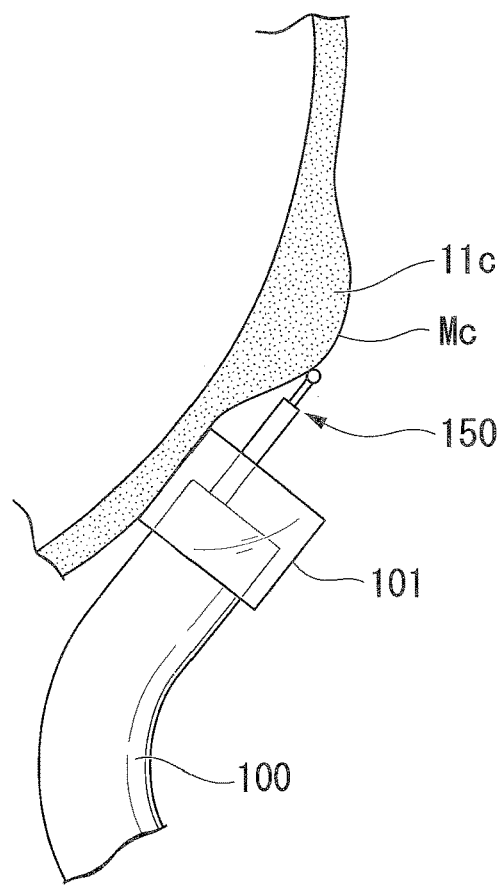
FIG. 6 is a view showing a state in which a treatment tool protruded from an endoscope is in contact with a portion close to a lesser curvature side of the treatment area.

Therefore, when using a high-frequency knife as the treatment tool 150, the treatment tool 150 is advanced along the mucous membrane Mc with the endoscope 100 fixed along the stomach wall as shown in FIG. 6, and cauterizing may be performed while retracting the treatment tool 150. When treatment is performed according to such a procedure, it is possible to suitably cauterize the mucous membrane using the discharge from the distal end of the treatment tool 150. This is an example of the cauterizing procedure, and cauterizing may be performed in other procedures. In FIG. 6, the cap 101 is attached to the distal end of the endoscope 100. Although the attachment of the cap 101 is not essential, the attachment of the cap allows the stomach wall to be pushed while maintaining a good view of the endoscope. As a result, the treatment instrument can be brought closer to the mucous membrane.

When cauterizing of the entire mucosal layer in the treatment area 10 is completed, the treatment area 10 becomes a damaged area where cauterizing is performed while the mucosal layer remains. The operator removes the endoscope and ends the procedure. After cauterizing, the entire treatment area may be observed with an endoscope and additional cauterizing may be performed according to the observation result.

Figure 7:
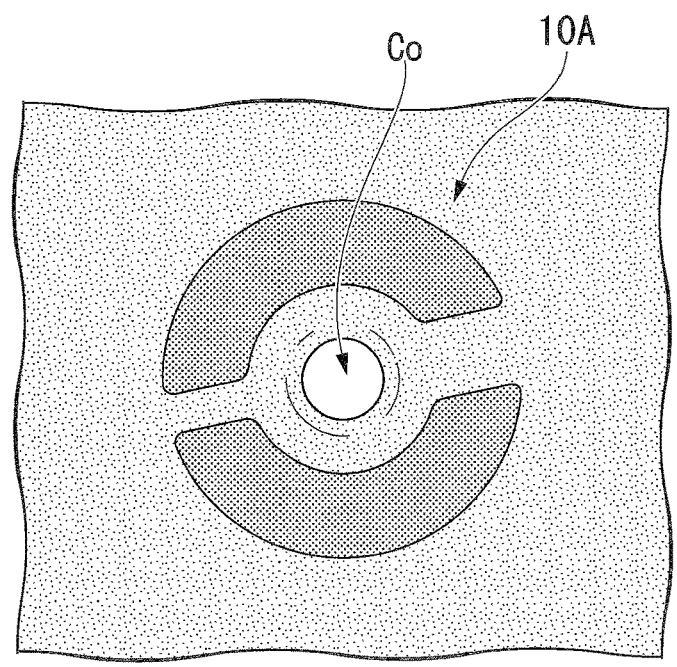
FIG. 7 is a diagram showing an example of the damaged area.

An example of the damaged area 10A after cauterizing is shown in FIG. 7. The mucosal layer in the damaged area 10A remains because it has not been excised. The gastric mucosa in the damaged area 10A is damaged to reach the mucosal base layer by cauterizing, and thereafter is regenerated through scarring. During regeneration of the mucous membrane, the gastric mucosa around the treatment area is drawn toward the treatment area by the reduction of the scar formed at the cauterized site. As a result, the gastric mucosa is bent at the first boundary portion 15 and the second boundary portion 16, and as shown in FIG. 8, the protruding pleats 111 and 112 extend in the circumferential direction of the gastroesophageal junction.

Figure 8:
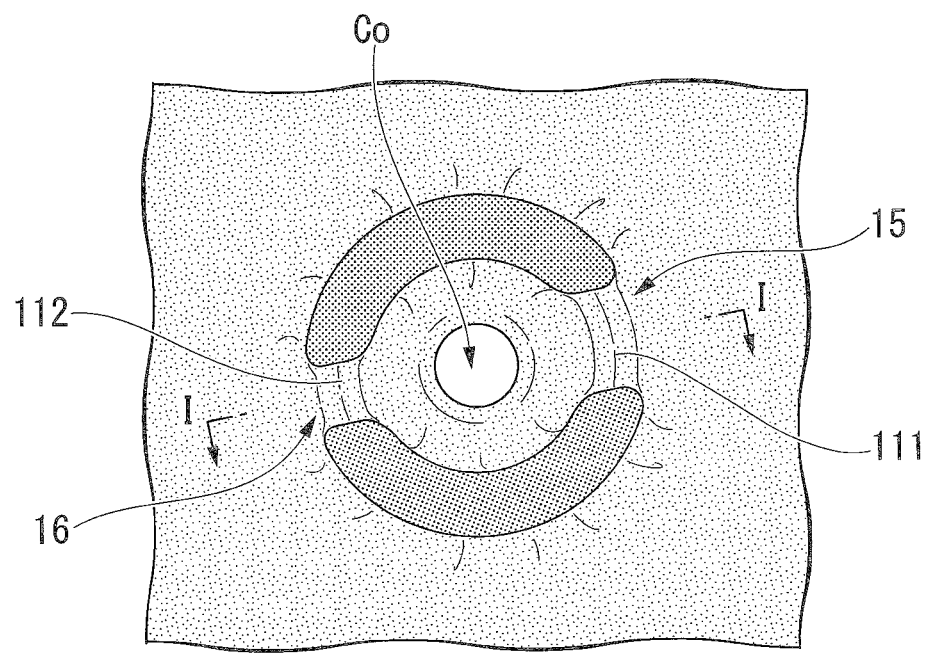
FIG. 8 is a view showing an example of an incomplete stenosis formed along with the restoration of the damaged area.
Figure 9:
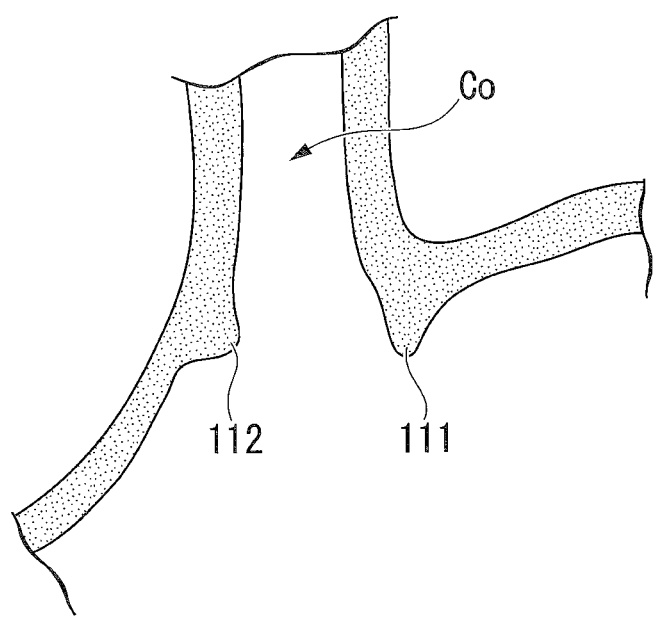
FIG. 9 is a cross-sectional view taken along the line I-I of FIG. 8.

FIG. 9 shows a schematic cross-sectional view taken along line I-I of FIG. 8. The pleats 111 form a His angle on the greater curvature side. The pleats 112 function as a valve to prevent backflow from the lesser curvature side. In the subject on which the treatment method is applied, incomplete stenosis is formed in the cardiac orifice by the pleats 111 and 112. As a result, reflux of the gastric contents is reduced and the symptoms of GERD are ameliorated.

As described above, the treatment method of the present embodiment can be performed simply by cauterizing the treatment area 10 using the endoscope 100 and the treatment tool 150 inserted from the natural opening, so it is easy to perform. The treatment method of the present embodiment can be performed only by bringing the distal end of the treatment tool 150 close to the mucous membrane, so the degree of difficulty of the procedure is low.

In addition, since cauterizing of the tissue in the stomach is performed and cauterizing of the esophagus is not performed, discomfort or the like at the time of swallowing due to a strong constriction in the esophagus is hard to occur.

The treatment method of the present embodiment can be implemented simply by bringing the treatment tool close to the mucous membrane to perform cauterizing, so it is easy to cauterize the operator's intended range.

In the procedure for excising the mucous membrane, if the therapeutic effect of GERD is not sufficient due to the form of scarring after excision or the like, it is difficult to perform the same treatment again on the site from which the mucous membrane was excised.

On the other hand, although the treatment method of the present embodiment damages the mucous membrane, it remains without excision, and therefore, it can be applied to a portion where the mucous membrane excision is difficult due to tissue fibrosis and the like. In the endoscopic observation of incomplete stenosis after a predetermined period of time, if the formation of the folds 111, 112, or the like is not sufficient, cauterizing can be performed again on the mucosal layer (step D). Therefore, it is possible to flexibly respond to retreatment or additional treatment according to the follow-up result.

Various parameters such as the shape, size, and degree of damage of the treatment area related to cauterizing after the follow-up may be the same as or different from the first treatment.

The treatment method of the present embodiment uses high-frequency coagulation developed for hemostasis as a treatment principle, so there is almost no risk of perforation of the stomach wall or bleeding after treatment. In the treatment method of the present embodiment, strict control of the injection amount of liquid for swelling and lifting up strictly controlled by a conventional procedure, the amount of air supplied into the stomach, or the like is not required, and this point is also simple.

In the treatment area 10, in addition to the first boundary portion 105 forming the His angle, the second boundary 106 exists as an undamaged area between the sub-areas 11 and 12. As a result, excessive narrowing is less likely to occur in the treatment area than in the case where the treatment area is annular or is a single area with a long extension.

As described above, although an embodiment was described, the technical scope is not limited to the the above embodiment. In the range which does not deviate from the scope of exemplary embodiments, it is possible to change the combination of components, make various changes to or delete each component. Although some modifications are illustrated below, these are not all, and other modifications are possible. Two or more of these changes may be combined as appropriate.

In the treatment method of the present embodiment, the order which performs cauterizing of a treatment area can be changed suitably. For example, cauterizing of portions 11a, 11b, and 11c may be performed in any order. Alternatively, cauterizing of the first area 11 and the second area 12 may be performed in parallel, or cauterizing of one of the first area 11 and the second area 12 may be performed before cauterizing of the other is performed.

Since the cauterizing in the treatment method of the present embodiment does not reach a muscle layer, the treatment method of the present embodiment can be performed even if swelling and lifting up is not performed. That is, step C may be omitted.

The digestive tract used as the object of the treatment method of the present embodiment is not restricted to a stomach, and it is applicable also to esophagus or the like. For example, when the subject to be treated has symptoms of esophageal mucosal hypersensitivity, or the like, part or all of the treatment area may be located in the esophagus.

When the treatment area is set in the esophagus, if the treatment is performed over the entire area of a certain area with no gap in the circumferential direction, excessive stenosis may occur. The possibility of causing excessive stenosis can be reduced by methods such as providing a non-treatment area in a circumferential direction, providing a non-treatment area in a helical shape, or providing a non-treatment area intermittently in the axial direction.

Moreover, the treatment method of the present embodiment is not only treatment of GERD which is dysfunction of esophagus, but can be applied to treatment of dysfunction of sphincter in other parts of digestive tract (for example, fecal incontinence which is dysfunction of anal sphincter, or the like).

Next, an embodiment of a treatment tool using the treatment method of the present invention will be described with reference to FIGS. 11 to 14.

Figure 11:
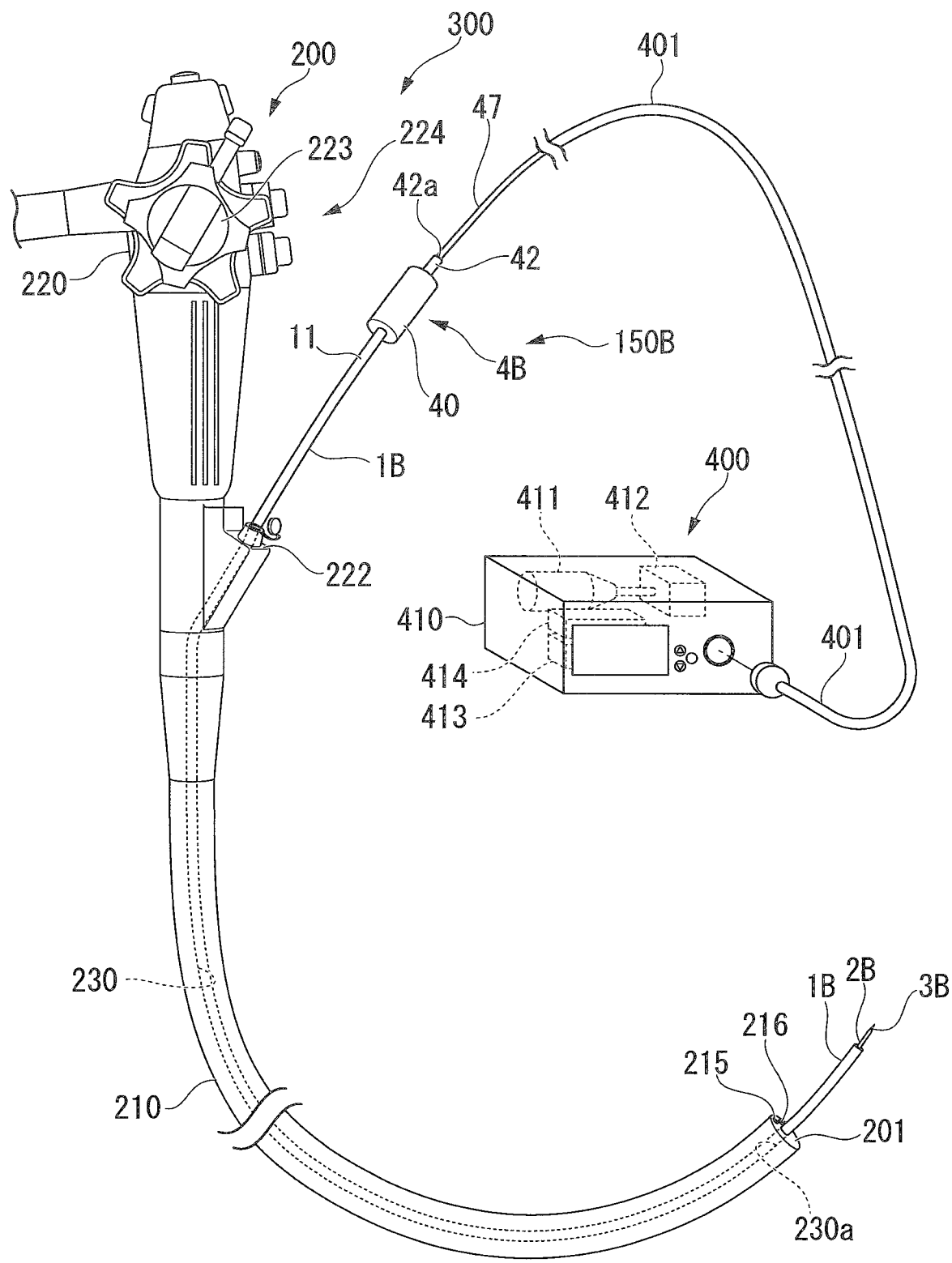
FIG. 11 is a diagram showing an overall configuration of an endoscope system including a treatment tool according to an embodiment of the present invention.

FIG. 11 is a diagram showing the overall configuration of the endoscopic treatment system 300 including the treatment tool 150B according to the present embodiment. The endoscopic treatment system 300 includes an endoscope 200 and a treatment tool 150B inserted into a channel of the endoscope 200.

The endoscope 200 is a known flexible endoscope, and includes a long insertion portion 210 and an operation portion 220 provided at a proximal end portion of the insertion portion 210. An imager 216 having a light guide 215 and a CCD or the like is provided at the distal end portion 201 of the insertion portion 210.

A channel 230 for inserting an endoscopic treatment tool such as the treatment tool 150B is formed in the insertion portion 210. A distal end portion 230a of the channel 230 is open at the distal end portion 201 of the insertion portion 210. A proximal end end of the channel 230 extends to the operating portion 220.

The insertion portion 210 is configured to be bendable in the vertical direction and the horizontal direction. The distal end of the operation wire is fixed to the distal end side of the insertion portion 210. The operating wire extends through the insertion portion 210 to the operating portion 220.

On the proximal end side of the operation portion 220, a knob 223 for operating the operation wire, a switch 224 for operating the imager 216, and the like are provided. The user can bend the insertion portion 210 in a desired direction by operating the knob 223.

An opening 222 communicating with the channel 230 is provided on the distal end end side of the operation portion 220. The user can insert an endoscopic treatment tool such as the treatment tool 150B from the opening 222.

As shown in FIG. 11, the treatment tool 150B can be attached to the treatment tool driving device 400 via the connector 401. The treatment tool driving device 400 includes a compressed gas source 411 filled with an inert gas such as argon gas inside the housing 410, a pressure regulator 412 that adjusts the pressure of the inert gas supplied from the compressed gas source 411 and supplies it to the treatment tool 150B, a high frequency power supply 413 that generates a high frequency current supplied to the treatment tool 150B, and a controller 414 that controls these in an integrated manner.

Figure 12:
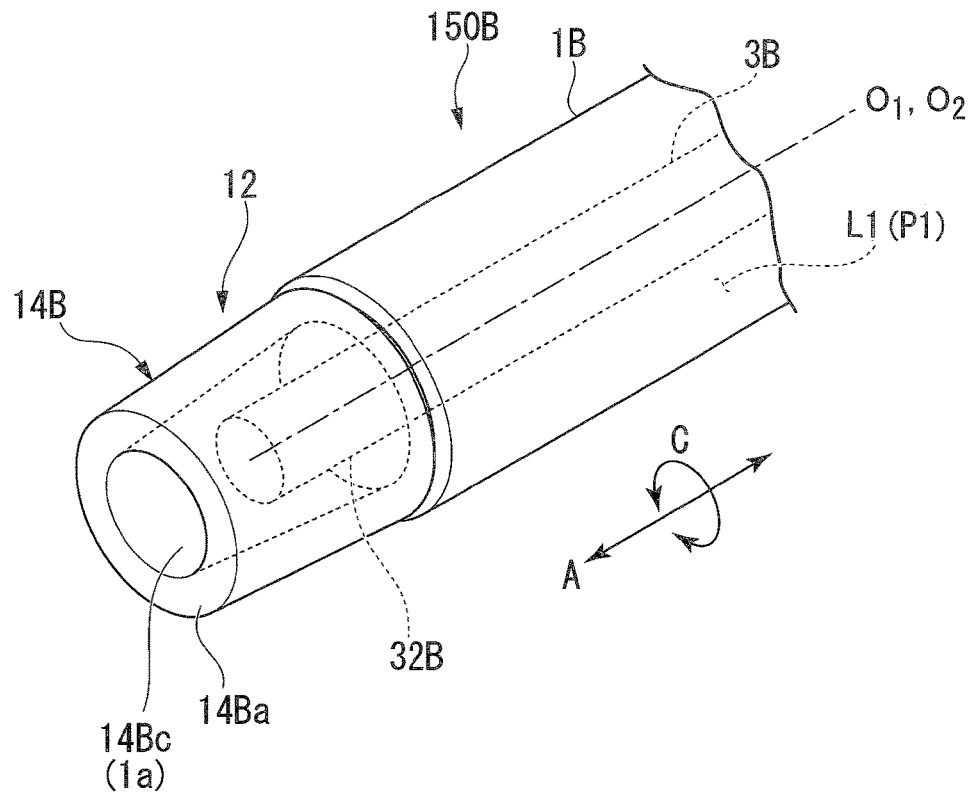
FIG. 12 is a perspective view of the distal end of the treatment tool.

FIG. 12 is a perspective view of the distal end of the treatment tool 150B.

The treatment tool 150B includes a gas pipeline 1B, an electrode 3B, and an operation portion 4B.

As shown in FIG. 12, the gas pipeline 1B is configured by a tubular member having an outer diameter through which the channel 230 of the endoscope 200 can be inserted. The tubular member is long and flexible. The internal space L1 of the gas pipeline 1B is a part of the gas flow path P1 through which an inert gas such as argon gas flows. The gas pipeline 1B is made of a material having electrical insulation such as PTFE (Poly Terra Fluoro Ethylene). The proximal end portion 11 of the gas pipeline 1B is attached to the operation portion 4B.

As shown in FIG. 12, the gas pipeline 1B has a distal end opening 14Bc at the distal end portion 12. The distal end opening 14Bc communicates with the internal space L1 of the gas pipeline 1B so that the inert gas can be discharged. The internal space L1 of the gas pipeline 1B extends along the longitudinal axis from the distal end opening 14Bc to the proximal end of the gas pipeline 1B. The inert gas injected from the gas supply port 42a flows through the internal space L1 of the gas pipeline 1B and is discharged from the distal end opening 14Bc of the gas pipeline 1B.

The electrode 3B is a wire-shaped member and is arranged in the internal space L1 of the gas pipeline 1B. The electrode 3B is made of a metal material, has conductivity, and can carry a high frequency current. The most proximal end of the proximal end portion 31 of the electrode 3B is connected to a high frequency power supply 413 that supplies a high frequency current. The distal end portion 32B of the electrode 3B is arranged in the vicinity of the distal end opening 14Bc in the internal space L1. More specifically, the distal end portion 32B of the electrode 3B is arranged in the distal end tip 14B, and the structure does not advance or retreat in the axial direction A. It is preferable that the central axis O2 of the electrode 3B substantially coincides with the central axis O1 of the gas pipeline 1B. Further, preferably, the distal end opening 14Bc of the distal end tip 14B is formed on the central axis O2 of the electrode 3B. Further, preferably, the inner diameter of the distal end opening 14Bc of the distal end tip 14B is larger than the outer diameter of the electrode 3B.

Figure 13:
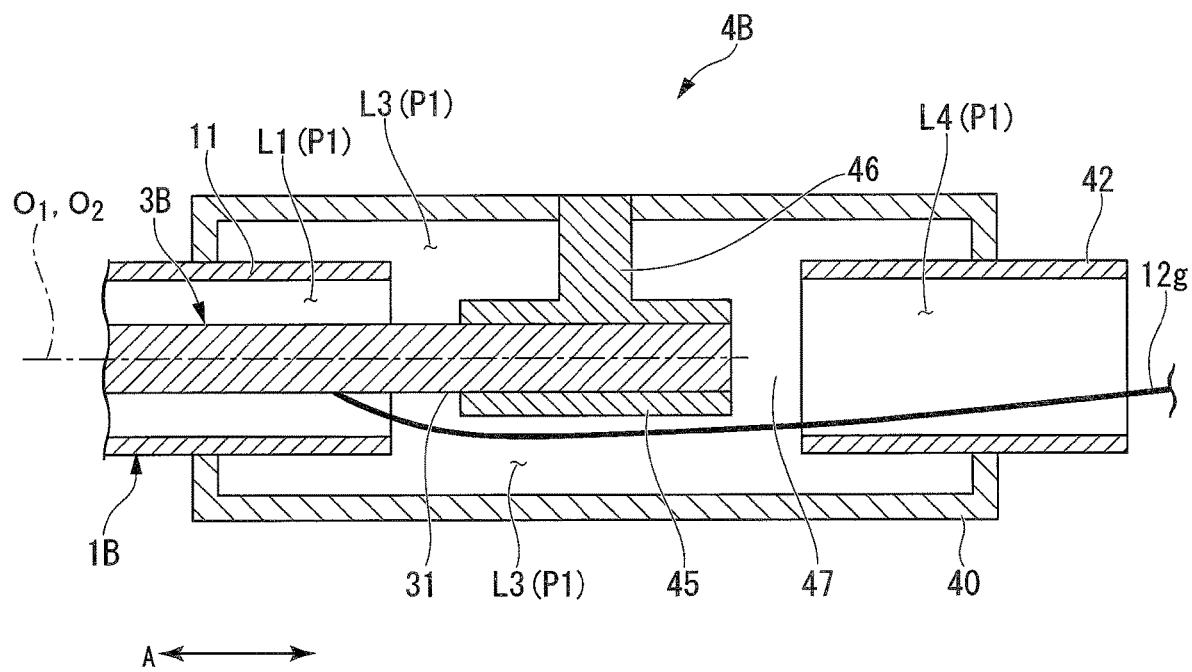
FIG. 13 is a cross-sectional view of an operation portion of the treatment tool.

FIG. 13 is a cross-sectional view of the operation portion 4B.

The operation portion 4B includes an operation portion main body 40 to which the proximal end portion 11 of the gas pipeline 1 is connected, and a gas supply pipeline 42. In the operation portion 4B, the proximal end portion 11 of the gas pipeline 1B and the proximal end portion 31 of the electrode 3B are fixed to the operation portion main body 40. The gas supply line 42 is a line for supplying an inert gas such as argon gas to the gas line 1 via the internal space of the operation portion main body 40. The gas supply port 42a provided at the proximal end of the gas supply line 42 is attached to the treatment tool driving device 400 via the connector 401.

Next, the operation of the treatment tool 150B of the present embodiment will be described. The treatment tool 150B can be used in combination with the endoscope 200 for the method of treating reflux esophagitis (GERD) described above.

Figure 14:
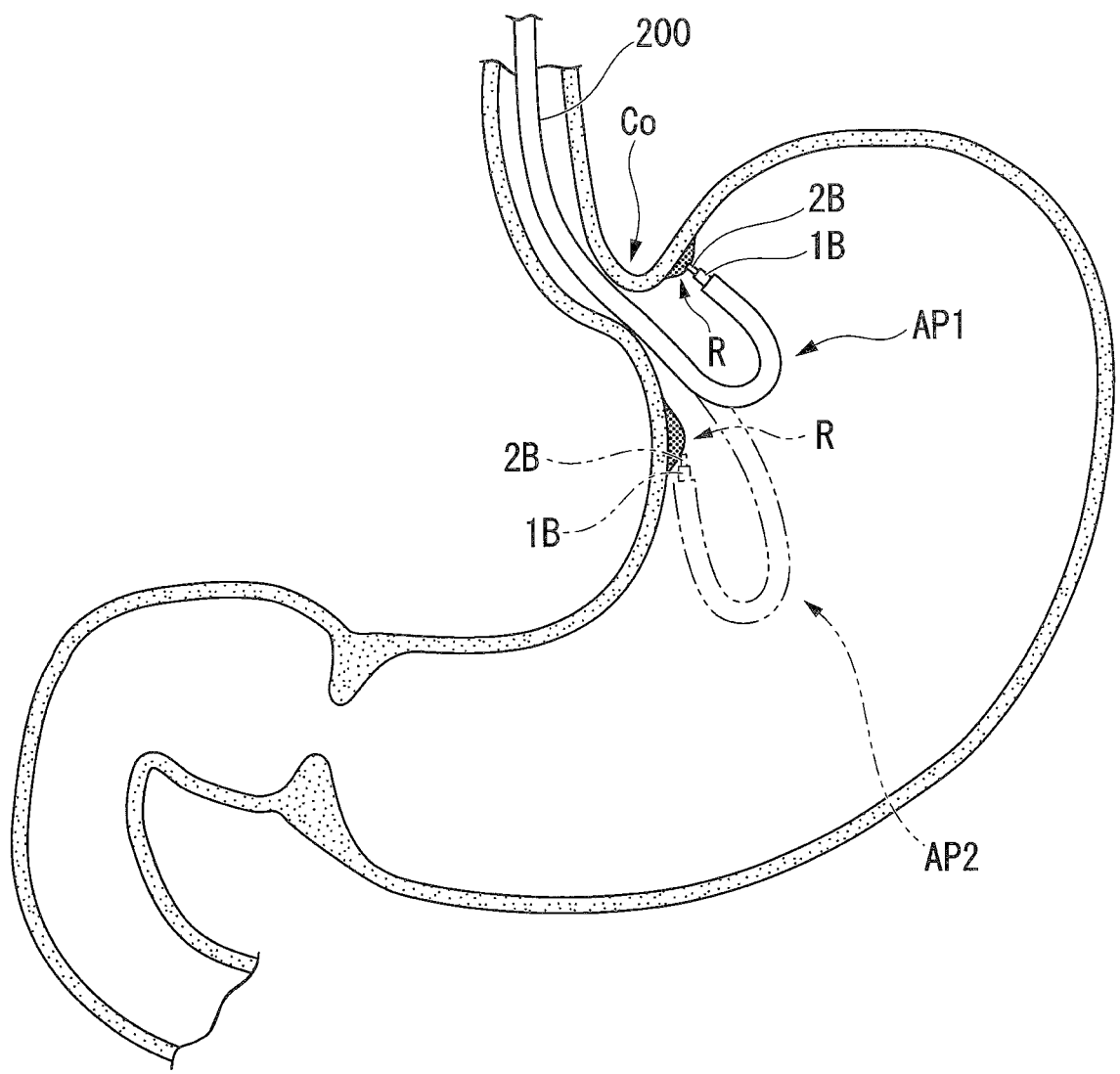
FIG. 14 is a diagram showing the treatment tool to be locally injected into the treatment area.

FIG. 14 is a diagram showing a treatment tool 150 to be locally injected into the specified treatment area R.

The operator specifies the treatment area R as described above (treatment area identification step). The operator bulges the mucosal layer of the treatment area R by locally injecting a liquid into the submucosal layer N of the identified treatment area R (local injection step). The method of locally injecting into the treatment area R includes a front approach AP1 and a tangential approach AP2.

The operator locally injects the liquid into the submucosal layer N of the treatment area R with a known local injection needle in the front approach AP1, and subsequently localizes the liquid into the submucosal layer N in the treatment area R in the tangential approach AP2. The order of the front approach AP1 and the tangential approach AP2 may be interchanged, and the front approach AP1 may be used for local injection after the tangential approach AP2 is used for local injection.

Then, the operator cauterizes the treatment area R (cauterizing step). At this time, the mucosa is not excised and only cauterizing is performed. The degree of cauterizing is such that the mucosal base layer M of the mucosa is damaged as described above.

In the front approach AP1, the operator arranges the treatment tool 150B so that the distal end opening 14Bc faces the treatment area R by moving the treatment tool 150B and/or the distal end portion 201 of the endoscope 200.

The operator supplies the inert gas to the gas supply port 42a. The supplied inert gas is discharged from the distal end opening 14Bc via the gas flow path P1. The operator cauterizes the treatment region R while supplying the inert gas in the vicinity of the treatment region R and supplying a high-frequency current to the electrode 3B. At that time, since the distal end portion 32B of the electrode 3B is located inside the distal end tip 14B, the electrode 3B and the treatment region R do not come into contact with each other.

By discharging the high-frequency current in the inert gas, the inert gas is ionized and becomes plasma P. The plasma P promotes stable maintenance of the discharge from the distal end portion 32B of the electrode 3B to the treatment region R via the distal end opening 14Bc.

After cauterizing the treated area R in the front approach AP1, the treated area R is subsequently cauterized in the tangential approach AP2. The operator cauterizes the treatment region R while supplying the inert gas in the vicinity of the treatment region R and supplying a high-frequency current to the electrode 3B. At that time, since the distal end portion 32B of the electrode 3B is located inside the distal end tip 14B, the electrode 3B and the treatment region R do not come into contact with each other.

The order of the front approach AP1 and the tangential approach AP2 may be interchanged, and the front approach AP1 may be cauterized after the tangential approach AP2 is cauterized.

What is claimed is:

1. An endoscopic treatment method comprising:
   inserting an endoscope into a digestive tract;
   forming a damaged area in at least a portion of the digestive tract along a circumferential direction by performing cauterizing while keeping a mucosal layer by observing with the endoscope; and
   forming an incomplete stenosis in the digestive tract, while restoring the damaged area,
   wherein the damaged area is formed by causing damage to a mucosal base layer, the mucosal base layer having an interface that contacts a submucosal layer.

2. The endoscopic treatment method according to claim 1, wherein the cauterizing includes discharging a high-frequency current into an inert gas.

3. The endoscopic treatment method according to claim 1, wherein
the digestive tract is a stomach;
the damaged area includes the mucosal layer of an inner wall of the stomach near a cardiac orifice;
a gap is provided between the damaged area and the cardiac orifice; and
the incomplete stenosis is formed around the cardiac orifice.

4. The endoscopic treatment method according to claim 3, wherein
the damaged area is formed only in the portion along the circumferential direction of the stomach.

5. The endoscopic treatment method according to claim 4, wherein
the damaged area includes:
an arcuate first area formed at an anterior wall of the stomach; and
an arcuate second area formed at a posterior wall of the stomach, wherein:
a first non-damaged area is positioned between the first area and the second area, and on a greater curvature side, the first non-damaged area being a first area where the mucosal layer is not cauterized,
a second non-damaged area is positioned between the first area and the second area, and on a lesser curvature side, the second non-damaged area being a second area where the mucosal layer is not cauterized, and
a dimension of the first non-damaged area in the circumferential direction is greater than a dimension of the second non-damaged area in the circumferential direction.

6. The endoscopic treatment method according to claim 3, further comprising:
before cauterizing the mucosal layer,
observing a junction between the stomach and esophagus with an endoscope inserted into the stomach, and identifying a treatment area to form the damaged area; and
forming a marking on at least a portion of a periphery of the treatment area.

7. The endoscopic treatment method according to claim 6, further comprising:
after forming the marking, infusing liquid into a submucosa of the treatment area to swell and lift up the treatment area.

8. The endoscopic treatment method according to claim 1, further comprising:
observing a condition of the incomplete stenosis generated in the digestive tract and additionally cauterizing the mucosal layer according to a result of the observation.

9. The endoscopic treatment method according to claim 1, wherein the mucosal layer is not excised.

* * * * *